United States Patent
Lee et al.

(10) Patent No.: US 8,968,796 B2
(45) Date of Patent: Mar. 3, 2015

(54) INGESTIBLE CANKER SORE TREATMENT

(71) Applicants: Plato Chun-Chih Lee, Chicago, IL (US); Arthur Joseph Dietrich, Chicago, IL (US)

(72) Inventors: Plato Chun-Chih Lee, Chicago, IL (US); Arthur Joseph Dietrich, Chicago, IL (US)

(*) Notice: Subject to any disclaimer, the term of this patent is extended or adjusted under 35 U.S.C. 154(b) by 0 days.

(21) Appl. No.: 14/047,442

(22) Filed: Oct. 7, 2013

(65) Prior Publication Data

US 2015/0024067 A1  Jan. 22, 2015

Related U.S. Application Data

(63) Continuation of application No. 13/945,085, filed on Jul. 18, 2013.

(51) Int. Cl.
| | | |
|---|---|---|
| *A61K 33/30* | (2006.01) | |
| *A61K 31/4415* | (2006.01) | |
| *A61K 31/519* | (2006.01) | |
| *A61K 31/714* | (2006.01) | |

(52) U.S. Cl.
CPC ............. *A61K 33/30* (2013.01); *A61K 31/4415* (2013.01); *A61K 31/519* (2013.01); *A61K 31/714* (2013.01)
USPC ........................................................ 424/715

(58) Field of Classification Search
CPC ..... A61K 8/04; A61K 8/673; A61K 31/4415; A61K 31/714; A61K 31/315
See application file for complete search history.

(56) References Cited

U.S. PATENT DOCUMENTS

| | | | |
|---|---|---|---|
| 5,028,311 A | | 7/1991 | Shigley et al. |
| 5,028,411 A | * | 7/1991 | Callingham et al. ............. 424/45 |
| 6,197,329 B1 | * | 3/2001 | Hermelin et al. .............. 424/441 |
| 2002/0061347 A1 | * | 5/2002 | Henry et al. .................... 426/74 |
| 2003/0012826 A1 | | 1/2003 | Giordano et al. |
| 2005/0058671 A1 | | 3/2005 | Bedding et al. |
| 2005/0208119 A1 | * | 9/2005 | Takemoto ..................... 424/450 |
| 2006/0074025 A1 | * | 4/2006 | Quay et al. ....................... 514/12 |
| 2006/0093705 A1 | * | 5/2006 | Mehansho et al. .............. 426/66 |
| 2006/0134020 A1 | * | 6/2006 | Robinson et al. ............... 424/52 |
| 2007/0128327 A1 | * | 6/2007 | Takashima et al. ........... 426/597 |
| 2010/0143554 A1 | | 6/2010 | Fukuda et al. |
| 2011/0135786 A1 | * | 6/2011 | Milici et al. ...................... 426/2 |

FOREIGN PATENT DOCUMENTS

| | | |
|---|---|---|
| CA | 2211382 A1 | 1/1998 |
| WO | 9206726 A1 | 4/1992 |

OTHER PUBLICATIONS

Lenntech BV; "Recommended daily intake of viatmins and minerals", Jun. 14, 2012, p. 1-2.*
Hotz, Christine, et al., "Zinc absorption from zinc oxide, zinc sulfate, zinc oxide + EDTA, or sodium-zinc EDTA does not differ when added as fortificants to maize tortillas". The Journal of Nutrition, 2005. vol. 135, pp. 1102-1105.

* cited by examiner

*Primary Examiner* — H. Sarah Park
(74) *Attorney, Agent, or Firm* — Bishop Diehl & Lee, Ltd.

(57) ABSTRACT

A treatment and prevention formulation for canker sores of the oral cavity including an aqueous alkaline solution having at least three B vitamins and zinc (provided as Zn (II) EDTA alkali metal salt) mixed therein and administered to a target area by a spray container. The vitamins are $B_6$, $B_9$ and $B_{12}$, but may include other vitamins as well. The formulation is totally non-toxic in chemical nature and non-offensive in odor to others, so it can be used anywhere and at any time and can be swallowed after use.

8 Claims, No Drawings

INGESTIBLE CANKER SORE TREATMENT

RELATED APPLICATIONS

This application is a continuation-in-part of copending U.S. application Ser. No. 13/945,085 titled "Ingestible Canker Sore Treatment" and filed on Jul. 18, 2013. The '085 application is hereby incorporated by reference.

TECHNICAL FIELD OF INVENTION

The present invention relates to canker sore treatment. More specifically, the invention relates to an ingestible canker sore treatment. Even more specifically, the invention relates to an ingestible spray for canker sore treatment.

BACKGROUND OF INVENTION

A canker sore (medically known as an "aphthous ulcer") is an ulceration of the inner mucosal membrane of the mouth, with occasional occurrence on the tongue and in the gum area. These ulcers cause discomfort at the very least, and often are a source of pain for afflicted persons, especially during eating and drinking. Individual sores typically last for one to two weeks, but recurrences can result in much longer afflictions. A large percentage of the population (approximately 20%-40%, depending on the survey) is known to have had at least one canker sore in their life and many have frequent recurrences of this painful medical condition.

Currently, the cause or causes of canker sores are not well-known. Accordingly, there are no medications that can permanently cure or even prevent canker sores. Instead, there are a few commercial medications which merely treat the symptoms of canker sores. Most of these medications, both over the counter (OTC) and prescription medicines, are aimed at reducing the pain caused by canker sores, while others claim to "promote healing" by cleansing the affected area. However, none are capable of actually healing or even preventing the occurrence of canker sores. There is great need for a product that both inhibits the development of canker sores in all areas of the mouth, including the tongue and gums, at an early stage, and promotes healing of canker sores once they develop.

The present composition and application methods address these and other problems associated with canker sores. Where others have failed to appreciate the source of the problem or have overlooked the solution, the present composition prevents and heals canker sores while providing advantages in simplicity and effectiveness.

BRIEF SUMMARY OF THE INVENTION

A composition for an ingestible canker sore treatment and a method for using the ingestible canker sore composition are disclosed. The composition and treatment methods are effective in both prevention and treatment of canker sores within a user's oral cavity.

Generally speaking, the composition is comprised of all non-toxic ingredients, including at least three different B vitamins, and zinc combined in an alkaline solution.

In a particular embodiment of the composition, three of the different B vitamins include $B_6$, $B_9$ and $B_{12}$ vitamins. However, similar or additional B vitamins may be used for other applications. Further, the zinc component is preferably delivered using a chemical compound composed of Zn (II) EDTA alkali metal salt. The alkaline solution is preferably composed of any suitable alkali metal carbonate or hydroxide.

In particular embodiments of the composition, weight percentage of the specified components of the said solution are preferably about 3 parts-per-million (ppm) of Vitamin $B_6$, 1 ppm of Vitamin $B_9$, 5 ppm of Vitamin $B_{12}$, 65 ppm of zinc in Zinc (II) EDTA alkali metal salt, 1000 ppm of methylcarboxycellulose in alkali metal salt and 1200 ppm of carbonate in alkali metal carbonate.

Natural flavoring(s) of any suitable type may be added to the composition in an amount to make the treatment even more pleasant for the user.

In a particular embodiment, the disclosed composition is provided in a spray bottle for dispersal into the user's oral cavity. Alternatively, the composition may be provided in a capped bottle as a drinkable mouthwash. Alternate delivery methods are possible.

As to a method for relieving, treating and preventing canker sores in a user's oral cavity, an ingestible medium of the composition disclosed is delivered to a user's oral cavity where it can be effectively moved to contact substantially the entirety of potentially afflicted areas for a suitable duration of time. Then, the ingestible treatment may be either dispelled from the mouth (i.e., spit out) or ingested.

In an alternate method, the ingestible medium may be directed to an affected area only using a focused spray or the like. Again, the residual solution can then be expectorated or ingested.

Additional aspects and advantages of the disclosed invention can best be understood from a review of the following detailed description of the invention.

DETAILED DESCRIPTION OF THE INVENTION

While this invention is susceptible of embodiments in many different forms, there will herein be described in detail a preferred embodiment of the invention with the understanding that the present disclosure is to be considered as an exemplification of the principles of the invention and is not intended to limit the broad aspect of the invention to any specific embodiments.

Although the exact cause or causes for canker sores are not well-known, a large population has suffered from this potentially painful condition. The flair up of a canker sore can make it painful for a person to speak, drink, swallow or eat, depending the location and size of the canker sores. For many individuals, repeat occurrences are frequent and unpredictable.

Various likely causes of canker sores have been proposed. A comparison of the more popular proposed causes points to a few commonly observed factors. One likely factor is a deficiency in the intake of vitamins, including $B_6$, $B_9$ and $B_{12}$, and minerals such as zinc. Another major factor that has been frequently cited as a cause of canker sores is stress. Still another cited factor for canker sore formation is trauma to the mouth, such as an accidental bite of the soft cheek tissue or the tongue. It is also believed that acidity can exacerbate the sores, which is why many medical professionals suggest canker sore sufferers avoid highly acidic food and drinks. While none of these factors alone may cause canker sores, the more factors present increases the likelihood of canker sore formation.

The present formulation is directed to an ingestible mouth spray that aims at inhibiting the development of canker sores at an early stage and at healing existing canker sores should they develop. The preferred composition is constituted totally of non-toxic chemical ingredients.

Generally speaking, the formulation includes the use of an alkaline solution as an effective treatment of canker sores. The preferred formula also contains at least three B vitamins, and zinc, as deficiencies in these vitamins and mineral are commonly-known hosting factors of canker sores. Most preferably, the B vitamins include vitamin $B_6$, $B_9$, and $B_{12}$, but may include additional B vitamins.

A preferred embodiment of the formula contains the following chemical ingredients and measures (in parts-per-million (ppm)) in an aqueous solution:

1. Carbonate: 1200 ppm in an alkali metal salt
2. Vitamin $B_6$: 3.0 ppm
3. Vitamin $B_9$: 1.0 ppm
4. Vitamin $B_{12}$: 5.0 ppm
5. Zinc: 65 ppm in Zinc (II) EDTA alkali metal salt
6. Methycarboxycellulose: 1000 ppm in methycarboxycellulose alkali metal salt, as a thickening agent
7. a natural flavoring chemical (such as peppermint): very minute amount, as needed Preferably, the alkali metal is sodium ($Na^{30}$), but may also be potassium ($K^+$), lithium ($Li^+$), or cesium ($Cs^+$). Further, the formula can be modified and the following ranges for the chemical ingredients are possible for alternate embodiments in an aqueous solution:

1. Carbonate: 12 to 12000 ppm in an alkali metal salt
2. Hydroxide: 17 to 17000 ppm in an alkali metal salt
3. Vitamin $B_6$: 0.0 to 5.0 ppm
4. Vitamin $B_9$: 0.0 to 5.0 ppm
5. Vitamin $B_{12}$: 0.0 to 15.0 ppm
6. Other B vitamins: 0.0 to 5.0 ppm
7. Zinc: 0.1 to 150 ppm in Zinc (II) EDTA alkali metal salt
8. Methylcarboxycellulose: 30-3000 ppm in alkali metal salt, as a thickening agent
9. a natural flavoring chemical (such as peppermint): 0.0 to as needed Due to the non-toxicity of the composition, it can be applied to and held in the mouth as often and as long as the user prefers. This in turn allows longer contact between the mucosal membrane of the user's mouth and the composition. A user could allow an optimal time for an effective chemical reaction between the ingredients and the tissue, including any canker sores. Afterward, the composition can be swallowed. This provides a significant advantage over non-ingestible treatments, such as mouthwashes—i.e., it is not necessary to spit it out. The fact that this product is ingestible greatly enhances the timing that this product can be conveniently used or applied—the user can carry the product in his/her handbag or briefcase and use it almost anytime and almost anywhere. No longer does treatment require a bathroom sink or the like. The product can be administered at the user's home while watching TV, at the user's office desk, in the airport without toting bags to the restroom, at the bus stop and on the bus, in a restaurant, and in an almost infinite number of other locations where it would be otherwise be inappropriate to dispel a mouthwash. More frequent and longer applications of the treatment lead to more effective prevention and treatment of canker sores.

Further, the chemical composition results in a product which is neutral in both taste and smell. As such, the use of the composition, even in intimate social gatherings, is not offensive to others and significantly reduces the occasions for missing a treatment.

In a preferred formulation, vitamin $B_6$ (pyridoxine, pyridoxal, or pyridoxamine, or pyridoxine hydrochloride), $B_9$ (folic acid), $B_{12}$ (various cobalamins; commonly cyanocobalamin in vitamin supplements) and zinc have been added to the alkaline solution to improve the intake of these components and reduce the cause of canker sores due to the deficiencies in these components. Other B vitamins, such as $B_1$ (thiamine), $B_2$ (riboflavin), $B_3$ (niacin or niacinamide), $B_5$ (pantothenic acid) and $B_7$ (biotin; vitamin H) may be substituted or added to other formulations, if desired.

The inclusion of zinc in a preferred formulation is due to the fact that, in scientific literature, Zinc has also been shown to be anti-ulceration and thus, will further help to reduce the likelihood of forming canker sores (ulceration of the mucous of the mouth).

Mental stress is believed to be a major and probably the most frequent contributing factor for the occurrence of canker sores. As much as stress is a psychological condition, it is however extremely import to realize that, this psychological condition does produce physiological changes. In 2012, Proceedings of National Academy of Sciences, USA, released a report that correlates stress and tissue inflammations. This strongly supports the long clinical observation that stress results in tissue inflammation. Inflammation biochemically results in acidosis of the body's tissues. There have been many studies which support the fact that under stress, many tissues/organs are more acidic than those of a control group. The ulcerations of the tissues come as a result of the prolonged stress and prolonged acidosis of the tissues, such as the mucous membranes of the mouth.

Trauma to the mouth, such as an accidental bite of the soft cheek or the tongue is believed to be another factor for the occurrences of canker sores. An unhealed injury to any tissues is known to incite the inflammation reactions from the body. Thus, just like mental stress, trauma to the mouth also results in the inflammations and acidosis of the injured tissues in the mouth, resulting in the formation of canker sores.

Many medical professionals suggest canker sore sufferers avoid highly acidic food and drinks. This clinical advice correlates well with the fact that canker sores, irrespective of the causes, are in principle results of the inflammation and the ensuing acidosis of the mucous tissues and extracellular acidity from the drinks or foods will only exacerbate the inflammation.

The disclosed formulation, therefore, directs to reverse the acidosis—and the possible ensuing ulcerations—of the mucous membranes of the mouth during early phases in the development of canker sores. Such treatment, as described, will result in prevention of and quicker healing of canker sores.

With the inclusion of Methylcarboxycellulose alkali metal salt, as a thickening agent, the preferred formulation is considered to be stable (for shelf-life consideration) and is a clear, non-toxic and ingestible alkaline solution. It is also very neutral and can be pleasant in taste, especially when a natural flavoring chemical is included. And, it has no offensive odor to others. The present embodiment can thus be applied in any work or social occasion without missing a dose.

The matter set forth in the foregoing description is offered by way of illustration only and not as a limitation. While particular embodiments have been described, it will be apparent to those skilled in the art that changes and modifications may be made without departing from the broader aspects of applicants' contribution. The actual scope of the protection sought is intended to be defined in the following claims when viewed in their proper perspective based on relevant prior art.

What is claim is:

1. An ingestible formulation for the treatment of canker sores, the formula consisting essentially of:
    at least three B vitamins comprising 0.1 to 5.0 ppm vitamin B6, 0.1 to 5.0 ppm vitamin B9, and 0.1 to 15.0 ppm vitamin B12;
    0.1 to 150 ppm zinc, as Zn (II) EDTA alkali metal salt; and
    an alkaline solution comprised of a suitable alkali metal carbonate with 120 to 12000 ppm in carbonate, and having a pH in the range of 11.1 to 11.5, wherein the B vitamins, and zinc are mixed in the solution.

2. An ingestible formulation for the treatment of canker sores, the formula consisting essentially of:
at least three B vitamins comprising 0.1 to 5.0 ppm vitamin B6, 0.1 to 5.0 ppm vitamin B9, and 0.1 to 15.0 ppm vitamin B12;
0.1 to 150 ppm zinc, as Zn (II) EDTA alkali metal salt; and
an alkaline solution comprised of a suitable alkali metal hydroxide with 17 to 17000 ppm in hydroxide, and having a pH in the range of 11.1 to 11.5, wherein the B vitamins, and zinc are mixed in the solution.

3. The ingestible formulation of claim 2, wherein the alkali metal hydroxide comprises sodium hydroxide.

4. The ingestible formulation of claim 1, wherein the alkali metal carbonate comprises sodium carbonate.

5. The ingestible formulation of claim 1, further comprising additional B vitamins in the range of from about 0.1 ppm to about 5.0 ppm.

6. The ingestible formulation of claim 1, further comprising a natural flavoring chemical.

7. The ingestible formulation of claim 1, wherein the alkali metal carbonate has a concentration of about 1200 ppm.

8. The ingestible formulation of claim 4, wherein the sodium carbonate has a concentration of about 1200 ppm.

* * * * *